(12) United States Patent
Soni et al.

(10) Patent No.: US 12,138,271 B2
(45) Date of Patent: *Nov. 12, 2024

(54) PHARMACEUTICAL COMPOSITIONS OF TESTOSTERONE

(71) Applicant: SLAYBACK PHARMA LLC, Princeton, NJ (US)

(72) Inventors: Umangi K. Soni, Telangana (IN); Prem Prakash Singh, Telangana (IN); Hanimi Reddy Bapatu, Telangana (IN); Praveen Kumar Subbappa, Princeton, NJ (US); Ajay Kumar Singh, Princeton, NJ (US)

(73) Assignee: SLAYBACK PHARMA LLC, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/299,493

(22) Filed: Apr. 12, 2023

(65) Prior Publication Data

US 2023/0248742 A1    Aug. 10, 2023

Related U.S. Application Data

(63) Continuation of application No. 17/696,319, filed on Mar. 16, 2022, now Pat. No. 11,642,355, which is a continuation of application No. 16/363,376, filed on Mar. 25, 2019, now Pat. No. 11,311,554.

(30) Foreign Application Priority Data

Apr. 4, 2018  (IN) .............................. 201841012805

(51) Int. Cl.
| | |
|---|---|
| *A61K 31/568* | (2006.01) |
| *A61K 9/00* | (2006.01) |
| *A61K 47/06* | (2006.01) |
| *A61P 5/26* | (2006.01) |

(52) U.S. Cl.
CPC .......... *A61K 31/568* (2013.01); *A61K 9/0019* (2013.01); *A61K 47/06* (2013.01); *A61P 5/26* (2018.01)

(58) Field of Classification Search
CPC .... A61K 31/568; A61K 9/0019; A61K 47/06; A61P 5/26
See application file for complete search history.

(56) References Cited

U.S. PATENT DOCUMENTS

| | | | |
|---|---|---|---|
| 3,051,624 | A | 8/1962 | Lozinski |
| 3,164,520 | A | 1/1965 | Huber |
| 7,718,840 | B2 | 5/2010 | Hubler et al. |
| 8,338,395 | B2 | 12/2012 | Hubler et al. |
| 2011/0039814 | A1 | 2/2011 | Huatan et al. |
| 2012/0076855 | A1 | 3/2012 | Bardani |
| 2014/0371186 | A1 | 12/2014 | Wang et al. |

FOREIGN PATENT DOCUMENTS

GB   1 569 286 A   6/1980

OTHER PUBLICATIONS

Depo®—Testosterone, testosterone cypionate injection, USP Giii, Pharmacia & Upjohn Co, Jul. 2018.
Depo®—Testosterone (testosterone cypionate injection, USP) Giii, Pfizer Inc, Apr. 13, 2015.
Sacha, G., et al., "Pre-filled syringes: a review of the history, manufacturing and challenges," Pharm. Dev. Technol., 2015, vol. 20, No. 1, pp. 1-11.

*Primary Examiner* — Shobha Kantamneni
(74) *Attorney, Agent, or Firm* — Birch, Stewart, Kolasch & Birch, LLP

(57) ABSTRACT

Stable pharmaceutical compositions are provided, comprising a pharmaceutically effective amount of testosterone or a pharmaceutically acceptable ester thereof, a pharmaceutically acceptable oil vehicle, and a stabilizing amount of benzyl alcohol, for example, about 1% to 3% weight/volume of benzyl alcohol. The present invention also provides a process for stabilizing testosterone-containing pharmaceutical compositions by ageing them at a temperature of about 20° C. to about 60° C. for at least 48 hours, e.g., prior to secondary packing and labeling. These compositions were stable over the shelf life of the product, without exhibiting crystal formation, even upon storing at temperatures of about 2° C. to about 8° C. Other aspects of the invention relate to methods for making such pharmaceutical compositions and methods of using such pharmaceutical compositions for hormone replacement therapy, e.g., in a male patient having a condition associated with symptoms of deficiency or absence of endogenous testosterone.

16 Claims, No Drawings

PHARMACEUTICAL COMPOSITIONS OF TESTOSTERONE

CROSS-REFERENCE TO RELATED APPLICATIONS

This application is a continuation of U.S. application Ser. No. 17/696,319, filed on Mar. 16, 2022, which is a continuation of U.S. application Ser. No. 16/363,376, filed on Mar. 25, 2019, now U.S. Pat. No. 11,311,554, issued on Apr. 26, 2022, and claims foreign priority to Indian Application No. IN 201841012805, filed on Apr. 4, 2018, the entire contents of all of which are expressly incorporated by reference into the present application.

FIELD OF THE INVENTION

The present invention relates to injectable pharmaceutical compositions comprising testosterone or a pharmaceutically acceptable ester thereof, at least one pharmaceutically acceptable oil vehicle, and about 10 to 30 mg/mL benzyl alcohol. The present invention also provides a process for stabilizing testosterone containing pharmaceutical compositions by ageing them at a temperature range of 20-60° C. for at least 48 hours, prior to packaging and labeling. These pharmaceutical compositions are suitable for injectable administration (e.g., subcutaneous or intramuscular), and are stable over the shelf life of the product.

Other aspects of the invention relate to methods for making such compositions, as well as methods of treatment using such compositions. The pharmaceutical compositions of the present invention may be used for replacement hormone therapy in a male having a condition associated with symptoms of deficiency or absence of endogenous testosterone.

BACKGROUND OF THE INVENTION

Testosterone cypionate is represented by the following structural formula (I):

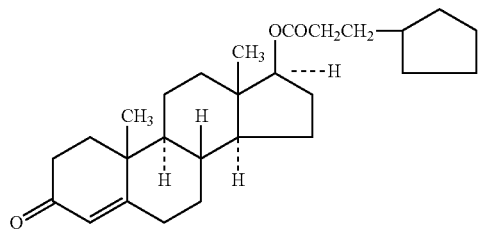

Testosterone cypionate is used in hormone replacement therapy in a male patient in need thereof, e.g., a male patient having a condition associated with symptoms of deficiency or absence of endogenous testosterone. Testosterone cypionate is the active ingredient of the commercial products such as DEPO-testosterone intramuscular depot injection.

DEPO-testosterone intramuscular depot injection is supplied as a sterile clear colourless to yellow solution in a single-use vial in 100 mg/ml and 200 mg/ml strengths. Each vial contains testosterone cypionate, cotton seed oil, benzyl benzoate and benzyl alcohol. The product may be administered by intramuscular injection, given deep in the gluteal muscle. The labeling notes that DEPO-testosterone intramuscular depot injection should be inspected visually for particulate matter and discoloration prior to administration, and states that warming and shaking the vial should re-dissolve any crystals that may have formed during storage at temperatures lower than room temperature 20° to 25° C. (68° to 77° F.).

U.S. Pat. No. 3,164,520 discloses compositions comprising testosterone ester of enanthate or palmitate medicaments and a physiological acceptable non-toxic pharmaceutical vehicle, comprised essentially of benzyl benzoate.

U.S. Pat. No. 7,718,640 describes pharmaceutical compositions comprising testosterone esters, particularly testosterone undecanoate, in a vehicle comprising castor oil and co-solvent, to achieve physiological normal serum levels of testosterone for an extended period of time.

GB 1569286 describes intramuscular injection comprising a hydrolyzable norethisterone oenanthate having progestational activity dissolved in an oily, unsaturated carrier which is a mixture of castor oil and benzyl benzoate. The carrier imparts a depot effect to the progestational activity for a desired period of time of at least several weeks. Lengthening of the depot effect occurs when volume of the injection solution is increased, while retaining the quantity of norethisterone oenanthate to be administered.

Current guidelines recommend that no more than 5 mL of liquid be injected intramuscularly in a single injection. Conventional testosterone cypionate intramuscular injection drug products may have crystals form in the vial when exposed to temperature less than room temperature. The label indicates that the vials must be observed for any crystal formation prior to administration. Administration of injection without proper observation causes an extreme pain at site of injection and may cause local tissue damage.

As such, there is a need for robust pharmaceutical compositions with small volumes, which avoid the problem of crystal formation during storage (e.g., when exposed to conventional storage temperatures), in order to improve patient compliance and convenience.

SUMMARY OF THE INVENTION

The present application describes stable, injectable compositions that not exhibit crystal formation under storage conditions, preferably even when stored for 6 months at 2° C. to about 8° C. In particular, the pharmaceutical composition according to the present application comprises a pharmaceutically effective amount of testosterone or a pharmaceutically acceptable ester thereof, such as testosterone cypionate. Preferably, the testosterone active ingredient is present at a concentration of about 100 mg/mL or a concentration of about 200 mg/mL.

In one embodiment, the present application relates to injectable pharmaceutical compositions comprising (i) testosterone or a pharmaceutically acceptable ester thereof, (ii) a pharmaceutically acceptable oil vehicle, and (iii) an effective amount of benzyl alcohol, e.g., more than about 1% weight/volume of benzyl alcohol, preferably from about 1% to about 3% weight/volume of benzyl alcohol. The pharmaceutical compositions according to this embodiment do not exhibit crystal formation for 6 months when stored at a temperature of about 2° C. to about 8° C. In certain preferred aspects, an effective amount of benzyl alcohol is sufficient that crystal formation is minimized and/or prevented, e.g., when the pharmaceutical compositions are stored immediately at about 10-15° C.

In one aspect, these pharmaceutical compositions comprise testosterone cypionate. In an aspect, the testosterone is present at a concentration of about 200 mg/mL. The pharmaceutically acceptable oil vehicle may be selected from the group consisting of cotton seed oil, castor oil, tea seed oil, sesame oil, linseed oil, peanut oil, olive oil, wheat-germ oil, and mixtures thereof. Certain preferred embodiments comprise more than about 10 mg/mL benzyl alcohol, and preferably about 10-25 mg/mL benzyl alcohol. The pharmaceutical compositions may further comprise benzyl benzoate, preferably at a concentration of about 220 mg/mL of benzyl benzoate.

In a preferred embodiment, the pharmaceutical compositions may comprise: about 200 mg/mL of testosterone cypionate; about 20 mg/mL to about 25 mg/mL of benzyl alcohol; about 224 mg/mL of benzyl benzoate; and cotton seed oil.

In certain aspects, the pharmaceutical compositions may further comprise an antioxidant in a stabilizing amount. For example, the pharmaceutical compositions may comprise a stabilizing amount of at least one pharmaceutically acceptable excipient, preferably selected from the group consisting of methionine, glycerol, propylene glycol, phenol, EDTA, BHT, and mixtures thereof.

The present application also provides certain methods for making the injectable pharmaceutical compositions, comprising: (i) heating a pharmaceutically acceptable oil vehicle, a sufficient amount of benzyl benzoate, and optionally, one or more pharmaceutically acceptable excipients, to form a first solution; (ii) adding a pharmaceutically effective amount of testosterone or a pharmaceutically acceptable ester thereof to the first solution to provide a second solution; and (iii) adding from about 1% to about 3% weight/volume benzyl alcohol to the second solution to provide a third solution. At this point, the process may include (iv) cooling the third solution, e.g., preferably to a temperature of about 20° C. to about 60° C., more preferably to a temperature of about 20° C. to about 25° C. These methods may also further comprise (v) filtering (e.g., passing the third solution through a suitable filter, such as a 0.22-micron filter) to provide a filtered solution; (vi) filling one or more containers with the filtered solution; (vii) optionally sealing the containers; and (viii) ageing the containers for at least 48 hours at a temperature of about 20° C. to about 60° C.

In another embodiment, the present invention also provides certain methods for preparing stable pharmaceutical compositions comprising: (i) providing a pharmaceutical composition comprising testosterone or a pharmaceutically acceptable salt or ester thereof, a pharmaceutically acceptable oil vehicle, and optionally, one or more pharmaceutically acceptable excipients; and (ii) ageing the composition for at least 48 hours at a temperature of about 20° C. to about 60° C. The present application also relates to pharmaceutical compositions produced according to this process. Advantageously, the pharmaceutical compositions according to this embodiment do not exhibit crystal formation for 6 months when stored at a temperature of about 2° C. to about 8° C. In certain preferred aspects, the pharmaceutical compositions further comprise an effective amount of benzyl alcohol, in an amount sufficient that crystal formation is minimized and/or prevented, e.g., when the pharmaceutical compositions are stored at about 10-15° C., or when the pharmaceutical compositions are stored at about 2-8° C.

In the embodiments of the present application, the pharmaceutical compositions may be filed into containers before or after the ageing step. For example, in some aspects, the pharmaceutical compositions may be filtered, filed into vials or pre-filled syringes, and then aged for at least 48 hours at a temperature of about 20° C. to about 60° C., prior to the final packaging and labelling of the finished drug products. Alternatively, the pharmaceutical composition may be aged, and then filtered, filled into containers, sealed and processed into the finished drug product.

In one aspect, these pharmaceutical compositions comprise testosterone cypionate. In an aspect, the testosterone is present at a concentration of about 200 mg/mL. The pharmaceutically acceptable oil vehicle may be selected from the group consisting of cotton seed oil, castor oil, tea seed oil, sesame oil, linseed oil, peanut oil, olive oil, wheat-germ oil, and mixtures thereof. The pharmaceutical compositions may further comprise benzyl benzoate. In certain aspects, the pharmaceutical compositions may further comprise an antioxidant in a stabilizing amount. For example, the pharmaceutical compositions may comprise a stabilizing amount of at least one pharmaceutically acceptable excipient, preferably selected from the group consisting of methionine, glycerol, propylene glycol, phenol, EDTA, BHT, and mixtures thereof. In a preferred embodiment, these pharmaceutical compositions may comprise: about 200 mg/mL of testosterone cypionate; about 20 mg/mL to about 25 mg/mL of benzyl alcohol; about 220 mg/mL to about 225 mg/mL of benzyl benzoate; and cotton seed oil.

The present application also relates to certain methods of treatment, comprising administering any of the pharmaceutical compositions described herein to a patient in need thereof, for replacement therapy in a patient having a condition associated with symptoms of deficiency or absence of endogenous testosterone.

DETAILED DESCRIPTION OF THE INVENTION

As used herein the term "testosterone" refers to the free base or a pharmaceutically acceptable ester, preferably testosterone cypionate (i.e., Testosterone 17β-cyclopentylpropionate). The term "pharmaceutically acceptable ester" may refer to any suitable ester, preferably an ester selected from the group of linear, branched and cyclic $C_3$-$C_{16}$ alkanoates, most preferably testosterone cypionate. By "linear and branched $C_3$-$C_{16}$ alkanoates" is meant aliphatic esters with chain lengths from 3 to 16 carbon atoms. In other aspects, the ester may be selected from the group consisting of acetate, caproate, cyclohexylpropionate, decanoate, enantate benzilic acid hydrazine, furoate, hexahydrobenzoate, hexahydrobenzylcarbonate, hexyloxyphenylpropionate, isobutyrate, isocaproate, ketolaurate, nicotinate, phenylacetate, phenylpropionate, phosphate, valerate, buciclate (20 Aet-1, CDB-1781), polyphloretin phosphate, 17β-(1-((5-(aminosulfonyl)-2-pyridinyl)carbonyl)-L-proline) (EC586), acetate butyrate, acetate propionate, benzoate, butyrate, diacetate, dipropionate, formate, isovalerate, palmitate, phenylbutyrate, stearate and sulfate. In certain preferred embodiments, the ester group is selected from the group consisting of cypionate, enantate, propionate and undecanoate. In certain aspects, the ester group is at the 17β-position of the testosterone molecule.

The term "pharmaceutically acceptable excipient" as used herein means a diluent, carrier, or composition auxiliary, which is non-toxic and inert, which does not have undesirable effects on a subject to whom it is administered and is suitable for delivering a therapeutically active agent to the target site without affecting the therapeutic activity of the said active agent. In certain embodiments, the pharmaceutical compositions may optionally contain pharmaceutically acceptable excipients, including antioxidants, buffers, preservatives, or stabilizing agents.

For purposes of the present invention, a pharmaceutically acceptable solvent is suitable for pharmaceutical use. In several embodiments of the invention, the pharmaceutically acceptable solvent is selected from group consisting of cotton seed oil, castor oil, tea seed oil, sesame oil, linseed oil, peanut oil, olive oil and wheat-germ oil. Within this aspect, the pharmaceutically acceptable solvent is preferably cotton seed oil.

In one embodiment, the present invention relates to stabilized liquid pharmaceutical compositions for intramuscular injection comprising testosterone, a pharmaceutical acceptable solvent, and a solubility enhancer.

In another embodiment, the present invention relates to stabilized liquid pharmaceutical compositions for intramuscular injection comprising (i) testosterone, (ii) a pharmaceutical acceptable solvent selected from group consisting of cotton seed oil, castor oil, tea seed oil, sesame oil, linseed oil, peanut oil, olive oil, wheat-germ oil and mixtures thereof, (iii) a solubility enhancer consisting of benzyl benzoate and (iv) benzyl alcohol.

In an aspect of the invention, the present invention relates to stabilized liquid pharmaceutical compositions for intramuscular injection comprising (i) testosterone, (ii) a pharmaceutical acceptable solvent, preferably cotton seed oil, (iii) a solubility enhancer consisting of benzyl benzoate and (iv) benzyl alcohol.

In an aspect of the invention, the present invention relates to stabilized liquid pharmaceutical compositions for intramuscular injection comprising (i) testosterone, (ii) a pharmaceutical acceptable solvent, preferably cotton seed oil, (iii) a solubility enhancer consisting of benzyl benzoate and (iv) benzyl alcohol, wherein benzyl alcohol is preferably in an amount of about 20 mg/ml to about 25 mg/ml.

In an aspect of the invention, the present invention relates to stabilized liquid pharmaceutical compositions for intramuscular injection comprising (i) testosterone, (ii) a pharmaceutical acceptable solvent, preferably cotton seed oil, (iii) a solubility enhancer consisting of benzyl benzoate and (iv) benzyl alcohol, wherein the benzyl alcohol is in an amount of about 20 mg/ml to about 25 mg/ml and the compositions have been aged for at least about 48 hours at a temperature from about 20° C. to about 60° C.

In certain embodiments, the present application relates to reducing or preventing formation of crystals in the pharmaceutical composition by using an effective amount of benzyl alcohol, and/or ageing the pharmaceutical composition prior to loading. One or both of these techniques may be used, and preferably, both techniques are used together.

As used herein, "ageing" or "holding" compositions refers to a process of storing compositions for at least 48 hours within a controlled temperature range, e.g., a temperature from about 20° C. to about 60° C. The temperature may be kept at a constant single temperature, or may vary slightly within this range. In an aspect of the invention, the present invention relates to aging compositions at a controlled temperature for at least about 48 hours, which will prevent or reduce crystal formation in the said compositions. In some embodiments, the pharmaceutical compositions are aged for an effective length of time, such as between 7-21 days, e.g., 7 days, 15 days, or 3 weeks. In a preferred embodiment, the pharmaceutical compositions are aged for at least 48 hours. The stabilized pharmaceutical compositions can then subsequently be further processed into the finished dosage form, or stored in vials, at suitable temperatures, e.g., 2-8° C. or at 10-15° C. By performing the initial ageing step, it is possible to prevent or reduce the problem of crystal formulation upon storage, e.g., even upon storing at a temperature of about 2° C. to about 8° C.

In another aspect of the invention, the present invention relates to compositions containing stabilizing amount of benzyl alcohol. In certain embodiments, an effective amount of benzyl alcohol is a concentration greater than about 10 mg/mL, and preferably a concentration from about 20 mg/mL to about 25 mg/mL. In certain embodiments, an effective amount of benzyl alcohol is about 15 mg/mL, about 20 mg/mL, about 25 mg/mL or about 30 mg/mL. In certain other embodiments, an effective amount of benzyl alcohol is a concentration greater than about 1% w/v, and preferably a concentration from about 1% w/v to about 3% w/v. When an effective amount of benzyl alcohol is used in the formulation, surprisingly, there is no crystal formation upon storage of the formulation, e.g., such as at room temperature for at least 48 hours or longer durations. By using an effective amount of benzyl alcohol for stabilization according to the invention, the problem with crystal formation can be minimized or avoided.

The pharmaceutical compositions may also comprise one or more pharmaceutically acceptable excipients. For example, the compositions may further comprise a preservative, an antioxidant, and/or a stabilizer. For example, the pharmaceutical compositions of the present invention may contain one or more antioxidants, preservatives, complexing agents and chelating agents such as, but are not limited to butylated hydroxyanisole (BHA), butylated hydroxyl toluene (BHT), citric acid, lactic acid, benzoic acid, tocopherol (Vitamin E), monothioglycerol, ascorbic acid, methyl paraben, benzyl alcohol, propyl gallate, surfactants, lipids, thioglycolic acid, niacinamide, nicotinic acid, creatine, cyclodextrins; ethylene diamine tetra acetic acid (EDTA), diethylenetriaminepentaacetic acid (DTPA), triethanolamine, 8-hydroxyquinoline, tartaric acid, phosphoric acid, gluconic acid, thiodipropionic acid, acetonic dicarboxylic acid, lecithin, di(hydroxyethyl)glycine, sorbitol, methionine, glycerol, propylene glycol, or phenol.

The present invention provides for a composition that may optionally comprise one or more preservatives. The term "preservative" refers to a substance present in a composition that can, at least in part, prevent and/or reduce decomposition of the composition. In some embodiments, the preservative may prevent and/or reduce decomposition of the composition by microbial growth in the composition. Preferably, the preservative is pharmaceutically acceptable.

For purposes of the present invention, preservatives for use in pharmaceutical compositions are known to those skilled in the art and include, but are not limited to, phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof.

In some embodiments, the preservative may be present in the composition at a concentration of in the range of about 1 to 10 mg/mL, preferably in the range of about 3 and 7 mg/mL, more preferably in the range of about 4 and 5 mg/mL, more preferably at about 4.5 mg/mL.

A pharmaceutically inert gas (e.g., which may be selected from nitrogen or carbon dioxide) may be bubbled into the solution to drive out oxygen. In certain aspects, rubber stoppers may be used for sealing the vials. Certain embodiments additionally relate to sterilizing the finished products, e.g., filtration through a bacterial-retaining filter, aseptic filling, terminal sterilization, incorporation of sterilizing agents, irradiation, and/or heating.

The finished dosage form may be provided in a sealed container (e.g., vials, pre-filled syringes, infusion bags, bottles, ampoules, etc.). In some embodiments, the container may be a single-dose formulation, or a multi-dose formulation. For example, a pre-filled syringe according to the invention may include single use auto injectors, or reusable auto injectors. In some embodiments, the same container may be used for multiple applications of the composition for up to about 10 days after initial use, preferably up to about 15 days, more preferably up to about 30 days, more preferably up to about 45 days, and most preferably up to about 60 days.

The pharmaceutical compositions incorporate a therapeutically effective amount of testosterone or a pharmaceutically acceptable ester thereof. In certain aspects of the invention, the testosterone concentration in the inventive compositions is from about 100 mg/mL to about 200 mg/mL, preferably about 100 mg/mL or about 200 mg/m L.

The present application also relates to certain methods of treatment, comprising administering any of the pharmaceutical compositions described herein to a patient in need thereof, for replacement therapy in a patient having a condition associated with symptoms of deficiency or absence of endogenous testosterone. Examples of diseases and symptoms associated with deficient endogenous levels of testosterone in a man may include primary hypogonadism (congenital or acquired), e.g., testicular failure due to cryptorchidism, bilateral torsion, orchitis, vanishing testis syndrome or orchidectomy, or hypogonadotropic hypogonadism (congenital or acquired), e.g., gonadotropin or LHRH deficiency, or pituitary-hypothalamic injury from tumors, trauma, or radiation. The compositions of the present application can be administered by suitable techniques, such as intramuscular injection deep in the gluteal muscle.

The dosage may be adjusted according to the patient's response and the appearance of adverse reactions. Various dosage regimens have been used to induce pubertal changes in hypogonadal males, e.g., by using lower dosages initially, gradually increasing the dose as puberty progresses, with or without a decrease to maintenance levels, or alternatively by using higher dosages to induce pubertal changes and lower dosages for maintenance after puberty. The chronological and skeletal ages must be taken into consideration, both in determining the initial dose and in adjusting the dose. For example, for replacement in the hypogonadal male, 50-400 mg may be administered every two to four weeks.

Suitable dosage amounts, dosage regimes, administration, and indications can be determined by the skilled artisan, based on the age, sex, and diagnosis of the individual patient, and are also known in the art, e.g., U.S. Pat. No. 7,718,640, which is hereby incorporated in its entirety.

EXAMPLES

The following examples are exemplary and not intended to be limiting. The above disclosure provides many different embodiments for implementing the features of the invention, and the following examples describe certain embodiments. Other modifications and methods known to one of ordinary skill in the art can also be applied to the following experimental procedures, without departing from the scope of the invention.

General HPLC Procedure

Analysis of samples for accelerated and long-term stability studies can be performed using high-performance liquid chromatography (HPLC). For example, the following HPLC procedure can be used to detect and quantify impurities of testosterone, as well as assay calculation. The materials and general conditions are listed below:

TABLE 1A

Chromatographic conditions for assay of testosterone cypionate

| | |
|---|---|
| Chromatographic mode | Gradient flow |
| Column | Zorbax SB C8, 50 × 4.6 mm, 3.5 μm (part no: 835975-906) |
| Wavelength | 254 nm |
| Flow rate | 1.5 mL/min |
| Injection volume | 20 μL |
| Column oven temperature | 40° C. |
| Sample cooler temperature | 5° C. |
| Run time | About 35 minutes |
| Mobile Phase A | 0.77 g of ammonium acetate dissolved in 1000 mL of water and filtered through 0.45 μm PVDF membrane filter |
| Mobile Phase B | Acetonitrile |

TABLE 1B

Gradient Program

| Time in minutes | % Mobile phase A | % Mobile phase B |
|---|---|---|
| 0 | 80 | 20 |
| 3 | 80 | 20 |
| 30 | 10 | 90 |
| 31 | 80 | 20 |
| 35 | 80 | 20 |

TABLE 2A

Chromatographic conditions for determining testosterone cypionate related substances

| | |
|---|---|
| Chromatographic mode | Gradient flow |
| Column | Xterra RP18, 150 × 4.6 mm, 3.5 μm |
| Wavelength | 254 nm |
| Flow rate | 1.0 mL/minutes |
| Injection volume | 10 μL |
| Column oven temperature | 40° C. |
| Sample cooler temperature | 5° C. |
| Run time | 60 minutes |
| Mobile Phase A | Add 0.5 mL of trifluoro acetic acid into 1000 mL of water |
| Mobile Phase B | Acetonitrile |

TABLE 2B

Gradient Program

| Time in minutes | % Mobile phase A | % Mobile phase B |
|---|---|---|
| 0 | 75 | 25 |
| 3 | 75 | 25 |
| 35 | 25 | 75 |
| 54 | 25 | 75 |
| 55 | 75 | 25 |
| 60 | 75 | 25 |

Example 1

TABLE 3

Preparation of Testosterone Cypionate composition, 200 mg/mL

| Ingredients | Qty/mL | % (w/v) | Qty/30 L batch |
|---|---|---|---|
| Testosterone cypionate, USP | 200 mg | 20.% | 6 kg |
| Benzyl benzoate | 224 mg | 22.4% | 6.72 kg |
| Cotton seed oil | 542.2 mg | 54.2% | 16.27 kg |
| Benzyl alcohol | 20 mg | 2% | 0.6 kg |
| Total | 986.2 mg | 98.6% | 29.59 kg |

Cotton seed oil and benzyl benzoate were added to the vessel and the mixture was heated to a temperature of about 40° C. to 60° C. Testosterone cypionate was added slowly, in lots, under stirring, for about 90 minutes, maintaining the solution temperature between about 40° C. to 60° C. The mixture was stirred for 60 minutes to ensure complete dissolution of testosterone cypionate. Benzyl alcohol was added slowly to the resultant solution at 40° C.-60° C., and continuously stirred for 30 minutes.

The above-obtained solution was cooled gradually to 23° C. over 3 hours. It was then filtered through a 0.22-micron PVDF filter into a buffer tank. The final solution was filled into USP Type I clear 2 mL glass vial or prefilled syringe with a target 1 mL fill volume. These vials and prefilled syringes were aged at a temperature of about 20° C. to about 30° C. for about 2-weeks, providing stabilized solutions. After aging, the stabilized solutions were then further processed into the final dosage form, e.g., proceeded with packaging and labelling the stabilized solutions.

Some of the above obtained vials and prefilled syringes were stored at a temperature of about 2° C. to about 8° C., and observed every two weeks for crystal formation.

TABLE 4

Stability observation for crystal formation

| Time (weeks) | 1 mL vial | 1 mL prefilled syringe |
|---|---|---|
| Initial | No crystals | No crystals |
| 4 | No crystals | No crystals |
| 12 | No crystals | No crystals |
| 26 | No crystals | No crystals |

Additional lots of the vials and prefilled syringes from Example 1 were also stored under accelerated (40° C.±2° C./75% RH±5% RH) and long-term (25° C.±2° C./60% RH±5% RH) stability conditions as per ICH stability requirements.

TABLE 5

Stability observations under accelerated conditions

| | 1mL vial | | | 1mL prefilled syringe | | |
|---|---|---|---|---|---|---|
| Test | Initial | 3 Months | 6 Months | Initial | 3 Months | 6 Months |
| % assay of Testosterone cypionate | 100.4% | 99.8% | 99.3% | 97.9% | 100% | 101.7% |
| Total impurities | 0.2% | 0.23% | 0.31% | 0.21% | 0.22% | 0.25% |
| Viscosity (in cps) | 50.5 | 48.7 | 50.9 | 50.3 | 50.3 | 50.9 |

TABLE 6

Stability observations under long term storage conditions

| | 1 mL vial | | 1 mL prefilled syringe | |
|---|---|---|---|---|
| Test | Initial | 6 months | Initial | 6 months |
| % assay of Testosterone cypionate | 97.9% | 100.1% | 100.4% | 98.4% |
| Total impurities | 0.21% | 0.28% | 0.21% | 0.31% |
| Viscosity (in cps) | 50.5 | 49.8 | 50.3 | 53.7 |

Example 2

TABLE 7

Preparation of Testosterone Cypionate composition with varying amounts of benzyl alcohol

| Ingredients | Composition A | Composition B | Composition C |
|---|---|---|---|
| | Quantity in (mg/mL) | | |
| Testosterone cypionate | 200 | 200 | 200 |
| Benzyl benzoate | 224 | 224 | 224 |
| Cotton seed oil | 556 | 542.20 | 535.60 |
| Benzyl alcohol | 9.45 | 20 | 25 |
| Total | 989.45 | 986.2 | 984.6 |

Manufacturing Procedure

1. The quantify of Benzyl benzoate shown in the above table was added to cotton seed oil in a glass beaker and stirred for 10 minutes while heating at 40° C.-45° C. to form a solution.
2. Testosterone cypionate was added to the above solution and stirred until the solution was clear. To this solution, benzyl alcohol was added, and stirred continuously for 10 minutes.
3. The solution volume was made up to 100 mL with cotton seed oil which was stirred for 60 minutes.
4. The bulk solution was filled into 10 mL tubular glass vials.

Example 3

Samples from Compositions A, B and C were tested under various conditions (e.g., either stored immediately, or aged at a certain temperature prior to storage), and then observed for crystal formation over time. These results are summarized in Tables 8-14 below.

TABLE 8

Observation for crystals in the composition A, B and C, when samples stored immediately at 10° C.-15° C.

| Day | Composition A | Composition B | Composition C |
|---|---|---|---|
| 0 (Initial) | Clear pale-yellow solution | Clear pale-yellow solution | Clear pale-yellow solution |
| 1 | Clear pale-yellow solution | Clear pale-yellow solution | Clear pale-yellow solution |
| 2 | Needle like crystals were observed | Clear pale-yellow solution | Clear pale-yellow solution |
| 3 | Vials withdrawn (Study discontinued) | Clear pale-yellow solution | Clear pale-yellow solution |

TABLE 8-continued

Observation for crystals in the composition A, B and C, when samples stored immediately at 10° C.-15° C.

| Day | Composition A | Composition B | Composition C |
| --- | --- | --- | --- |
| 50 | | Clear pale-yellow solution | Clear pale-yellow solution |
| 120 | | Clear pale-yellow solution | Clear pale-yellow solution |

Samples from Composition A, B and C were loaded or stored immediately at a temperature range of 10° C.-15° C. after preparation (e.g., without being held at a specific temperature). Composition A shows needle like crystals within 2 days from loading. Composition B and C were free from crystals for 3 months.

TABLE 9

Observation for crystals in the compositions A, B and C when samples which were initially aged for 7 days at controlled temperature ranges 20° C. to 25° C. and then stored at 10° C.-15° C.

| Day | Composition A | Composition B | Composition C |
| --- | --- | --- | --- |
| 0 (Initial) | Clear pale-yellow solution | Clear pale-yellow solution | Clear pale-yellow solution |
| 1 | Clear pale-yellow solution | Clear pale-yellow solution | Clear pale-yellow solution |
| 11 | Clear pale-yellow solution | Clear pale-yellow solution | Clear pale-yellow solution |
| 21 | Clear pale-yellow solution | Clear pale-yellow solution | Clear pale-yellow solution |
| 31 | Clear pale-yellow solution | Clear pale-yellow solution | Clear pale-yellow solution |
| 41 | Clear pale-yellow solution | Clear pale-yellow solution | Clear pale-yellow solution |
| 44 | Clear pale-yellow solution | Clear pale-yellow solution | Clear pale-yellow solution |
| 120 | Clear pale-yellow solution | Clear pale-yellow solution | Clear pale-yellow solution |

Samples from Composition A, B and C were initially held for 7 days at controlled temperature ranges 20° C. to 25° C. and then stored at 10° C.-15° C. Composition A, B and C were free from crystals throughout the entire study.

TABLE 10

Observation for crystals in the composition A, B and C when samples were initially aged for 15 days at controlled temperature ranges 20° C. to 25° C. and then stored at 10° C.-15° C.

| Day | Composition A | Composition B | Composition C |
| --- | --- | --- | --- |
| 0 (Initial) | Clear pale-yellow solution | Clear pale-yellow solution | Clear pale-yellow solution |
| 1 | Clear pale-yellow solution | Clear pale-yellow solution | Clear pale-yellow solution |
| 10 | Clear pale-yellow solution | Clear pale-yellow solution | Clear pale-yellow solution |
| 21 | Clear pale-yellow solution | Clear pale-yellow solution | Clear pale-yellow solution |
| 30 | Clear pale-yellow solution | Clear pale-yellow solution | Clear pale-yellow solution |
| 37 | Clear pale-yellow solution | Clear pale-yellow solution | Clear pale-yellow solution |
| 120 | Clear pale-yellow solution | Clear pale-yellow solution | Clear pale-yellow solution |

Samples from Composition A, B and C were initially aged for 15 days at controlled temperature ranges 20° C. to 25° C. and then stored at 10° C.-15° C. Compositions A, B and C were free from crystals for 3 months.

TABLE 11

Observation for crystals in the compositions A, B and C when samples were initially aged for 3 weeks at controlled temperature ranges 20° C. to 25° C. and then stored at 2° C. to 8° C.

| Day | Composition A | Composition B | Composition C |
| --- | --- | --- | --- |
| 0 (Initial) | Clear pale-yellow solution | Clear pale-yellow solution | Clear pale-yellow solution |
| 1 | Slight needle like crystals observed | Clear pale-yellow solution | Clear pale-yellow solution |
| 2 | Product freezes | Clear pale-yellow solution | Clear pale-yellow solution |
| 3 | Vials withdrawn (Study discontinued) | Clear pale-yellow solution | Clear pale-yellow solution |
| 10 | | Clear pale-yellow solution | Clear pale-yellow solution |
| 20 | | Clear pale-yellow solution | Clear pale-yellow solution |
| 29 | | Clear pale-yellow solution | Clear pale-yellow solution |
| 120 | | Clear pale-yellow solution | Clear pale-yellow solution |

Samples from Composition A, B and C were initially aged for 3 weeks at controlled temperature ranges 20° C. to 25° C. and then stored at 2° C.-8° C. Composition A shows needle like crystals within one day and the sample was frozen on the second day from loading. Compositions B and C were free from crystals for 3 months.

TABLE 12

Observation for crystals in the composition A, B and C when samples were initially aged for 1 week at controlled temperature ranges 20° C. to 25° C. and then stored at 2° C. to 8° C.

| Day | Composition A | Composition B | Composition C |
| --- | --- | --- | --- |
| 0 (Initial) | Clear pale-yellow solution | Clear pale-yellow solution | Clear pale-yellow solution |
| 1 | Needle like crystals observed | Clear pale-yellow solution | Clear pale-yellow solution |
| 3 | Product freezes | Clear pale-yellow solution | Clear pale-yellow solution |
| 4 | Vials withdrawn (Study discontinued) | Clear pale-yellow solution | Clear pale-yellow solution |
| 10 | | Clear pale-yellow solution | Clear pale-yellow solution |
| 20 | | Clear pale-yellow solution | Clear pale-yellow solution |
| 23 | | Clear pale-yellow solution | Clear pale-yellow solution |
| 120 | | Clear pale-yellow solution | Clear pale-yellow solution |

Samples from Compositions A, B and C were initially aged for 1 week at controlled temperature ranges 20° C. to 25° C. and then stored at temperatures between about 2° C. to 8° C. Composition A shows needle like crystals within a day and the sample was frozen on the third day. Composition B and C were free from crystals up to 3 months.

TABLE 13

Observation for crystals in the composition B and C when samples were not aged, and stored immediately at 2° C. to 8° C.

| Day | Composition B | Composition C |
| --- | --- | --- |
| 0 (Initial) | Clear pale-yellow solution | Clear pale-yellow solution |
| 1 | Clear pale-yellow solution | Clear pale-yellow solution |
| 2 | Clear pale-yellow solution | Clear pale-yellow solution |

TABLE 13-continued

Observation for crystals in the composition B and C when samples were not aged, and stored immediately at 2° C. to 8° C.

| Day | Composition B | Composition C |
| --- | --- | --- |
| 5 | Needle like crystals observed | 2-3 weak needle like crystals observed at bottom, not clearly visible |
| 10 | Significant growth of crystals observed | Crystal growth observed, but less compared to Composition B |
| 14 | | |

Samples from Compositions A, B and C were stored immediately at temperatures between about 2° C. to 8° C. without any ageing. Compositions B and C were observed to have needle like crystals on the fifth day.

TABLE 14

Observation for crystals in the composition B and C when samples were initially aged for 2 days at controlled temperature ranges 20° C. to 25° C. and then stored at 2° C. to 8° C.

| Day | Composition B | Composition C |
| --- | --- | --- |
| 0 (Initial) | Clear pale-yellow solution | Clear pale-yellow solution |
| 10 | Clear pale-yellow solution | Clear pale-yellow solution |
| 13 | Clear pale-yellow solution | Clear pale-yellow solution |
| 150 | Clear pale-yellow solution | Clear pale-yellow solution |

Samples from Composition B and C were initially aged for 2 days at controlled temperature ranges 20° C. to 25° C. and then stored at temperatures between about 2° C. to 8° C. Compositions B and C were free from crystals for up to 5 months.

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

The invention claimed is:

1. An injectable pharmaceutical composition comprising:
 a. about 200 mg/mL testosterone cypionate;
 b. about 15 mg/mL to 30 mg/mL benzyl alcohol;
 c. benzyl benzoate; and
 d. cotton seed oil;
 wherein the testosterone cypionate is the only hormonally active ingredient in the pharmaceutical composition and present in a therapeutically effective amount;
 wherein the composition is sterilized and suitable for intramuscular injection; and
 wherein the composition does not exhibit crystal formation for 6 months when stored at a temperature of about 10° C. to about 15° C.

2. The injectable pharmaceutical composition according to claim 1, wherein the composition comprises about 220 mg/mL to about 225 mg/mL of benzyl benzoate.

3. The injectable pharmaceutical composition according to claim 1, wherein the composition comprises about 540 mg/mL of cotton seed oil.

4. The injectable pharmaceutical composition according to claim 1, wherein the composition comprises about 220 mg/mL to about 225 mg/mL of benzyl benzoate and about 540 mg/mL of cotton seed oil.

5. The injectable pharmaceutical composition according to claim 1, wherein the concentration of benzyl alcohol is 20 mg/mL.

6. The injectable pharmaceutical composition according to claim 1, wherein the concentration of benzyl alcohol is 25 mg/mL.

7. The injectable pharmaceutical composition according to claim 1, wherein the composition is provided in a sealed container.

8. The injectable pharmaceutical composition according to claim 7, wherein the sealed container is a vial or a pre-filled syringe.

9. An injectable pharmaceutical composition comprising:
 a. about 200 mg/mL testosterone cypionate;
 b. about 15 mg/mL to 30 mg/mL benzyl alcohol;
 c. benzyl benzoate; and
 d. cotton seed oil;
 wherein the testosterone cypionate is the only hormonally active ingredient in the pharmaceutical composition and present in a therapeutically effective amount;
 wherein the composition is sterilized and suitable for intramuscular injection; and
 wherein the composition has been aged for at least 48 hours at a temperature of about 20° C. to about 60° C. prior to storage and wherein the composition does not exhibit crystal formation for 6 months when stored at a temperature of about 2° C. to about 8° C.

10. The injectable pharmaceutical composition according to claim 9, wherein the composition comprises about 220 mg/mL to about 225 mg/mL of benzyl benzoate.

11. The injectable pharmaceutical composition according to claim 9, wherein the composition comprises about 540 mg/mL of cotton seed oil.

12. The injectable pharmaceutical composition according to claim 9, wherein the composition comprises about 220 mg/mL to about 225 mg/mL of benzyl benzoate and about 540 mg/mL of cotton seed oil.

13. The injectable pharmaceutical composition according to claim 9, wherein the concentration of benzyl alcohol is 20 mg/mL.

14. The injectable pharmaceutical composition according to claim 9, wherein the concentration of benzyl alcohol is 25 mg/mL.

15. The injectable pharmaceutical composition according to claim 9, wherein the composition is provided in a sealed container.

16. The injectable pharmaceutical composition according to claim 15, wherein the sealed container is a vial or a pre-filled syringe.

* * * * *